(12) United States Patent
Ma et al.

(10) Patent No.: US 10,050,213 B2
(45) Date of Patent: Aug. 14, 2018

(54) BICARBAZOLE DERIVATIVE, PREPARATION PROCESS AND USE THEREOF, AND ORGANIC LUMINESCENT DEVICE

(71) Applicants: BOE Technology Group Co., Ltd., Beijing (CN); JiLin OLED Material Tech. Co., LTD., Changchun (CN)

(72) Inventors: Lifei Ma, Beijing (CN); Xiaoyu Ma, Beijing (CN); Hui Wang, Beijing (CN); Lujiang Huangfu, Beijing (CN)

(73) Assignees: BOE TECHNOLOGY GROUP CO., LTD., Beijing (CN); JILIN OLED MATERIAL TECH. CO., LTD., Changchun (CN)

( * ) Notice: Subject to any disclaimer, the term of this patent is extended or adjusted under 35 U.S.C. 154(b) by 316 days.

(21) Appl. No.: 14/415,005

(22) PCT Filed: May 30, 2014

(86) PCT No.: PCT/CN2014/078945
§ 371 (c)(1),
(2) Date: Jan. 15, 2015

(87) PCT Pub. No.: WO2015/085729
PCT Pub. Date: Jun. 18, 2015

(65) Prior Publication Data
US 2015/0349274 A1 Dec. 3, 2015

(30) Foreign Application Priority Data
Dec. 10, 2013 (CN) .......................... 2013 1 0670340

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 401/14* | (2006.01) | |
| *C07D 403/14* | (2006.01) | |
| *H05B 33/20* | (2006.01) | |
| *H01L 51/50* | (2006.01) | |

(52) U.S. Cl.
CPC ........ *H01L 51/0072* (2013.01); *C07D 401/14* (2013.01); *C07D 403/14* (2013.01); *C09K 11/06* (2013.01); *H01L 51/0067* (2013.01); *H05B 33/20* (2013.01); *C09K 2211/1007* (2013.01); *C09K 2211/1029* (2013.01); *C09K 2211/1044* (2013.01); *C09K 2211/1059* (2013.01); *H01L 51/0081* (2013.01); *H01L 51/0085* (2013.01); *H01L 51/506* (2013.01); *H01L 51/5016* (2013.01); *H01L 51/5056* (2013.01); *H01L 51/5088* (2013.01)

(58) Field of Classification Search
CPC .... H05B 33/20; C07D 209/82; C07D 401/00; C07D 401/02; C07D 401/04; C07D 401/14; C07D 403/00; C07D 403/02; C07D 403/04; C07D 403/14; C09K 11/06; C09K 2211/00; C09K 2211/10; C09K 2211/1003; C09K 2211/1007; C09K 2211/1018; C09K 2211/1029; C09K 2211/1044; C09K 2211/1059; H01L 51/0032; H01L 51/005; H01L 51/0051; H01L 51/0062; H01L 51/0067; H01L 51/0071; H01L 51/0072; H01L 51/0081; H01L 51/0085; H01L 51/50; H01L 51/5012; H01L 51/5016; H01L 51/5088; H01L 51/5056
USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| | | | | |
|---|---|---|---|---|
| 2006/0186796 A1* | 8/2006 | Yabe | ..................... | C07D 213/06 313/504 |
| 2009/0230846 A1* | 9/2009 | Yabe | ....................... | C09K 11/06 313/504 |
| 2011/0278555 A1* | 11/2011 | Inoue | ................... | C07D 209/82 257/40 |
| 2012/0223295 A1* | 9/2012 | Inoue | ..................... | C09K 11/06 257/40 |

FOREIGN PATENT DOCUMENTS

| | | | | |
|---|---|---|---|---|
| CN | 102421772 A | 4/2012 | | |
| CN | 103664909 A | 3/2014 | | |
| JP | WO 2012108881 A1 * | 8/2012 | ......... | H01L 51/0085 |
| JP | 2013-35752 A | 2/2013 | | |
| WO | 2012/023947 A1 | 2/2012 | | |

OTHER PUBLICATIONS

Okada et al. Dalton Trans. 2005, 1583-1590. Year of publication: 2005.*
International Search Report and Written Opinion (in Chinese) for PCT Application No. PCT/CN2014/078945, dated Aug. 8, 2014, 9 pages.

* cited by examiner

*Primary Examiner* — Andrew K Bohaty
(74) *Attorney, Agent, or Firm* — Westman, Champlin & Koehler, P.A.

(57) ABSTRACT

The invention provides a bicarbazole derivative represented by formula (I), wherein A is a group represented by formula (II), and wherein X, Y and Z represent a carbon atom or a nitrogen atom, and at least one of X, Y and Z represent a nitrogen atom. The invention further provides a process for preparing the compound. The invention further provides an organic electroluminescent device comprising the compound. This compound can be used as a phosphorescence host material, a hole-injecting material or a hole-transporting material in an organic electroluminescent device.

6 Claims, No Drawings

BICARBAZOLE DERIVATIVE, PREPARATION PROCESS AND USE THEREOF, AND ORGANIC LUMINESCENT DEVICE

CROSS-REFERENCE TO RELATED APPLICATION

This Application is a Section 371 National Stage Application of International Application No. PCT/CN2014/078945, filed 30 May 2014, which has not yet published, which claims priority to Chinese Application No. 201310670340.0, filed Dec. 10, 2013, in Chinese, the contents of which are hereby incorporated by reference in their entirety.

FIELD OF THE INVENTION

The invention relates to the field of organic electroluminescent materials, especially, a bicarbazole derivative, the preparation process and use thereof, and an organic luminescent device.

BACKGROUND OF THE INVENTION

An organic electroluminescent (EL) device (hereinafter, briefly referred to as "organic EL device") is generally composed of two opposite electrodes and at least one layer of an organic light-emitting compound inserted between these two electrodes. Electric charges are injected into an organic layer formed between the anode and the cathode in order to form electron hole pairs, so that an organic compound having fluorescent or phosphorescent characteristics generates light emission.

The research on the organic EL material started in 1950 when Bernanose observed light emission in the case where high current and voltage are applied to a polymer thin film containing organic pigments. In 1965, Pope et al. for the first time discovered the electroluminescent property of anthracene single crystal. In 1987, Tang et al. from Kodak Company discovered that even at a low voltage of 10V or less, an organic light-emitting device, which is formed from an organic material and has laminated separate functional layers, can provide a high luminance of 1000 cd/cm$^2$ or more.

In an organic material, the hole mobility is significantly higher than the electron mobility, so holes and electrons can be more effectively transported to the light-emitting layer when a hole transport layer and an electron transport layer are properly used. Additionally, when a balance between the hole density and the electron density in the light-emitting layer is achieved, the luminous efficiency can be improved.

When an electron and a hole recombine in an organic molecule, due to different manners of electron spin symmetry, two forms of excited state will occur. One is the form of a singlet excited state formed by a ground state electron with asymmetric spin, which releases energy in the form of fluorescence and then returns to the ground state; the other is the form of a triplet excited state formed by a ground state electron with symmetric spin, which releases energy in the form of phosphorescence and then returns to the ground state. According to theoretical speculation, the ratio of the singlet excited state to the triplet excited state caused by the recombination of electric charges is 1:3. If the energy of the singlet excited state is transferred to the triplet excited state for emitting phosphorescence, the internal quantum efficiency thereby may be close to 100%.

Generally, the phosphorescence host luminescent materials such as the carbazole ring compounds (e.g. CBP, etc.), and the phosphorescence guest luminescent materials such as a compound adhered with iridium (Ir), platinum (Pt) or the like as a central metal atom, are widely used. However, this kind of organic EL device has a short life of only 150 hours. Because CBP has a very low glass transition temperature of only 110° C. and possibly crystallizes, it is not suitable for commercial use.

SUMMARY OF THE INVENTION

In order to solve the above technical problem, the invention provides a compound which may be used as a green phosphorescence host material, a hole-injecting material or a hole-transporting material. The compound has an improved electrical stability, a better charge-transporting capability, a high glass transition temperature and does not crystallize.

The present invention further provides an organic electroluminescent (EL) device comprising the compound of the invention which has a low voltage, a high efficiency, a high luminance, a long life and a high stability.

The present invention provides a bicarbazole derivative represented by formula (I):

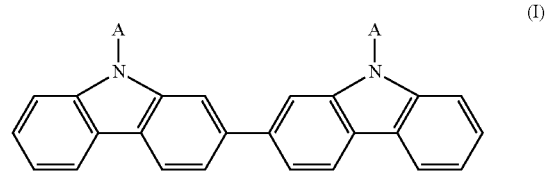

wherein A is a bicarbazole derivative-containing group represented by the following formula (II):

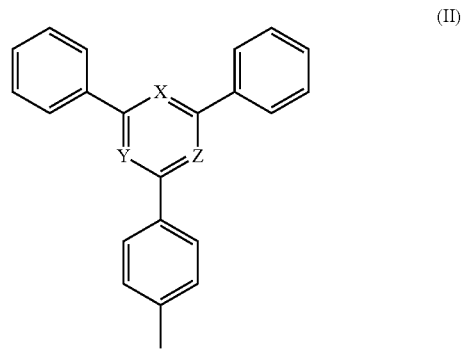

wherein X, Y and Z represent a carbon atom or a nitrogen atom, and at least one of X, Y and Z represents a nitrogen atom. Preferably, Z represents a nitrogen atom. More preferably, X and/or Y represent a nitrogen atom.

The preferable examples of the bicarbazole derivative of the invention are selected from the compounds represented by the following chemical structural formulas 001-004:

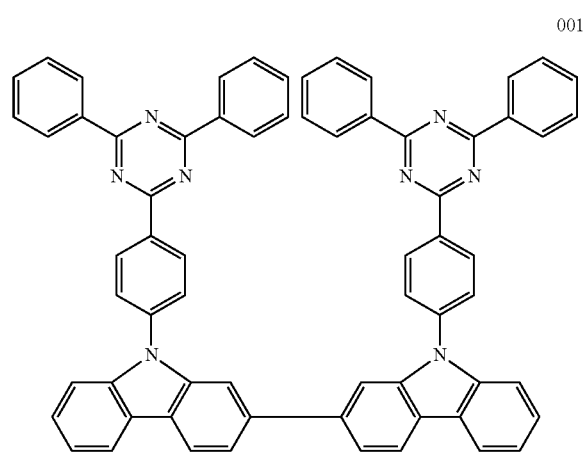
001
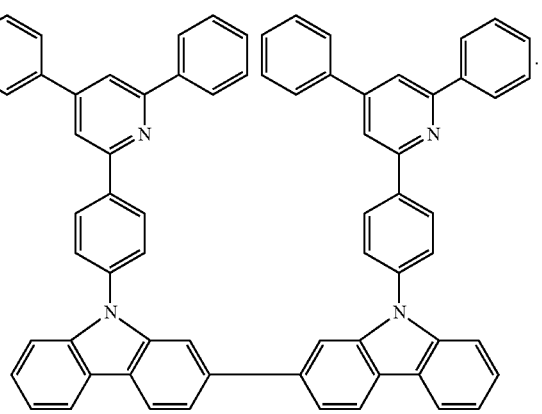
004
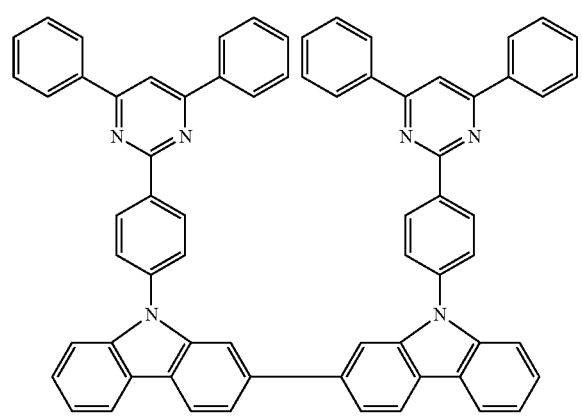
002
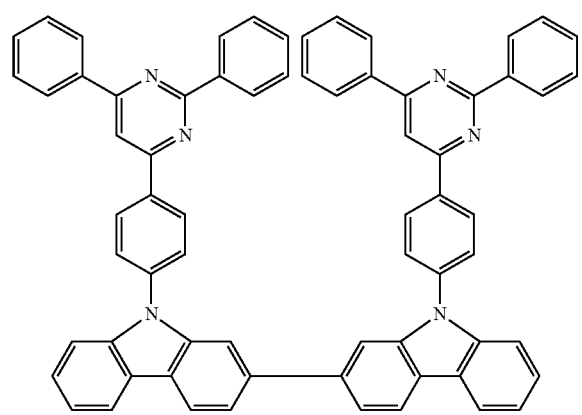
003
The invention further provides a process for preparing the bicarbazole derivative represented by formula (I), comprising a step of reacting a compound represented by formula (III)
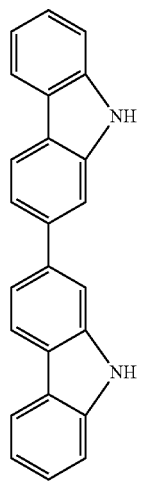
(III)
with a compound represented by formula (IV)
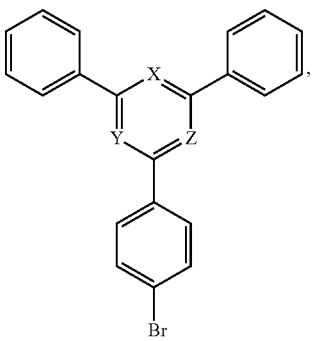
(IV)
wherein X, Y and Z have the same definitions as those in formula (II).

Preferably, the reaction is carried out in the presence of a catalyst. More preferably, the catalyst is palladium acetate and tri-tert-butylphosphine.

The invention further provides an organic electroluminescent device, comprising a first electrode, a second electrode and one or more organic compound layer(s) provided between the first electrode and the second electrode, wherein at least one organic compound layer comprises at least one compound represented by the formula (I). Preferably, the compound represented by the formula (I) is a phosphorescence host material.

The invention further provides use of the compound represented by the formula (I) in an organic electroluminescent device as a phosphorescence host material, a hole-injecting material or a hole-transporting material.

The bicarbazole derivative provided in the invention has an improved electrical stability, a better charge-transporting capability, a high glass transition temperature and does not crystallize. The organic electroluminescent device using the bicarbazole derivative exhibits a high efficiency, a high luminance, a long life, and has the advantage of lower manufacturing cost. Additionally, the life of the organic electroluminescent device is extended and the manufacturing cost of the organic electroluminescent device is reduced.

DETAILED DESCRIPTION OF THE INVENTION

The present invention provides a bicarbazole derivative represented by formula (I):

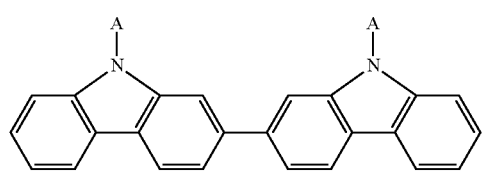

(I)

wherein A is a bicarbazole derivative-containing group represented by the following formula (II):

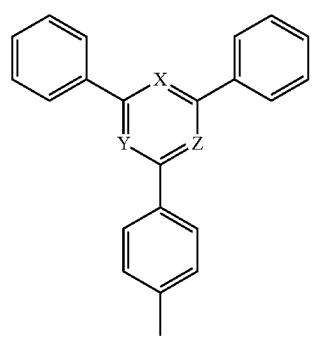

(II)

wherein X, Y and Z represent a carbon atom or a nitrogen atom, and at least one of X, Y and Z represents a nitrogen atom. Preferably, Z represents a nitrogen atom. More preferably, X and/or Y represent a nitrogen atom.

The preferable bicarbazole derivative is one of the compounds represented by the following formulas 001-004:

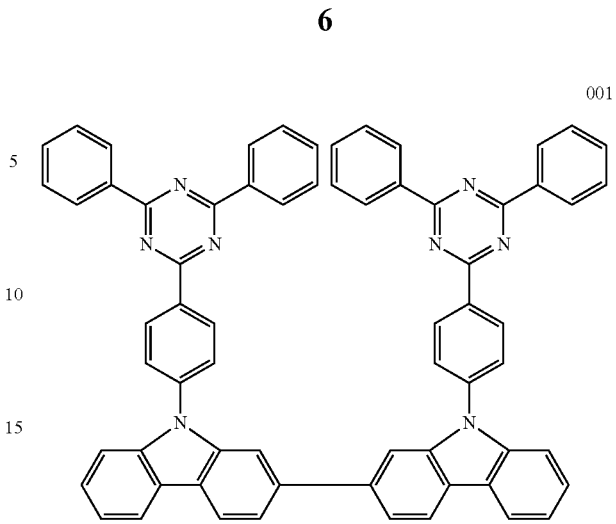

001

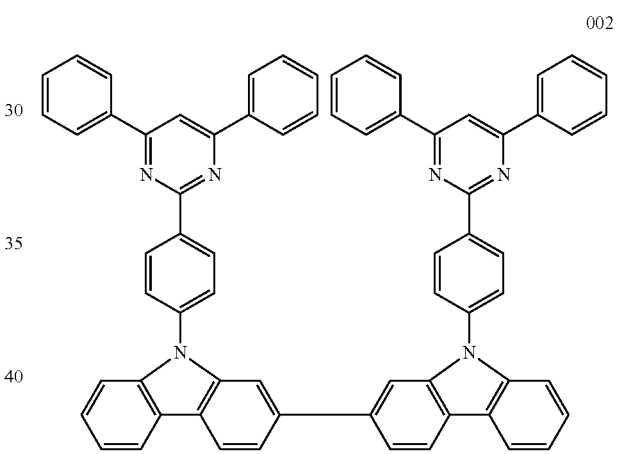

002

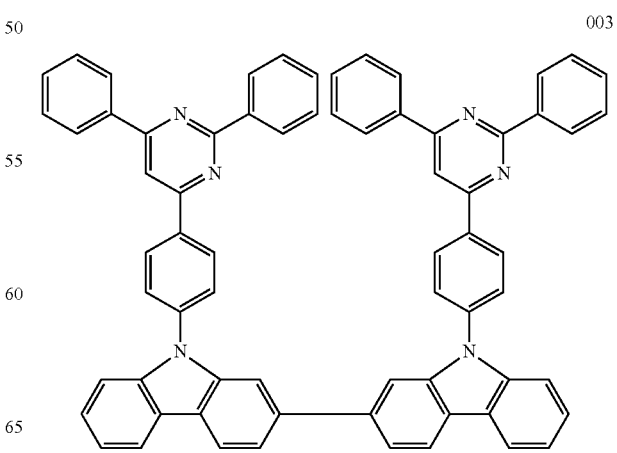

003

-continued

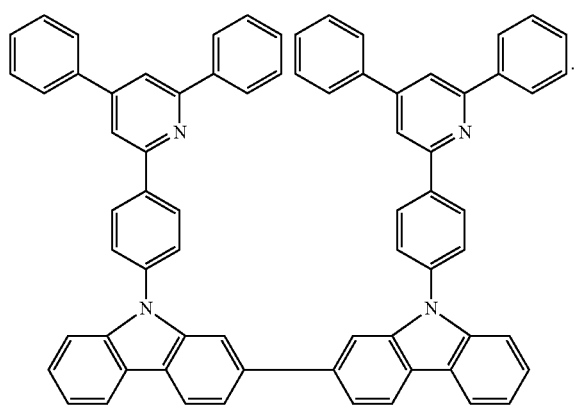

004

The invention further provides a process for preparing the bicarbazole derivative represented by formula (I), comprising a step of reacting a compound represented by formula (III)

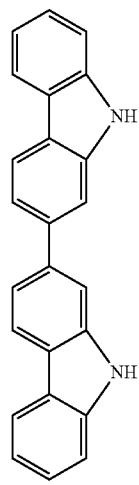

(III)

with a compound represented by formula (IV)

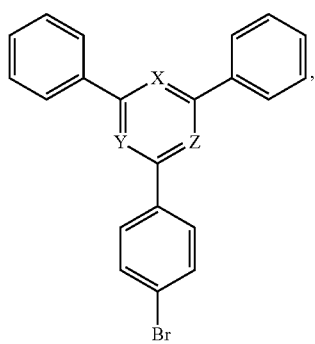

(IV)

wherein X, Y and Z have the same definitions as those in formula (II).

Preferably, the reaction is carried out in the presence of a catalyst. More preferably, the catalyst is palladium acetate and tri-tert-butylphosphine.

More preferably, the compound represented by formula (I) in the invention can be prepared from the following steps:

Step S1: adding bicarbazole (that is, the compound represented by formula (III)), a bromide of the A group (that is, the compound represented by formula (IV)), potassium tert-butoxide, a solvent and a catalyst into a degassed reaction container;

Step S2: increasing the reaction temperature and refluxing, performing the reaction sufficiently;

Step S3: performing filtration, purification, recrystallization and drying to obtain the compound represented by formula (I).

Here, the solvent is preferably toluene. The reaction temperature is preferably 110° C.

The present invention is described in more detail by the following examples. However, the following examples are only to illustrate the present invention more specifically, and the scope of the present invention is not limited to the examples. According to the user, the following examples may be modified and changed within the scope of the present invention.

Preparation Example 1: The Synthesis of Compound 001

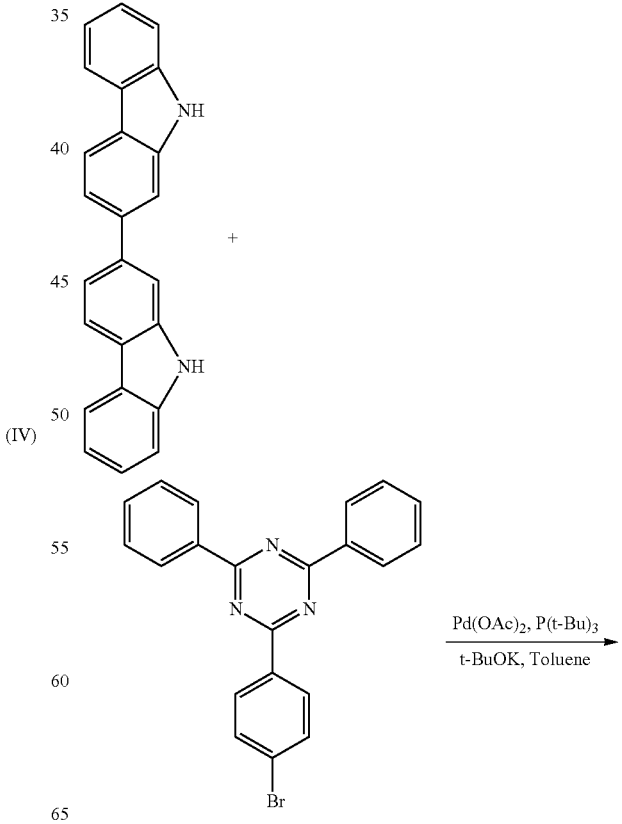

-continued

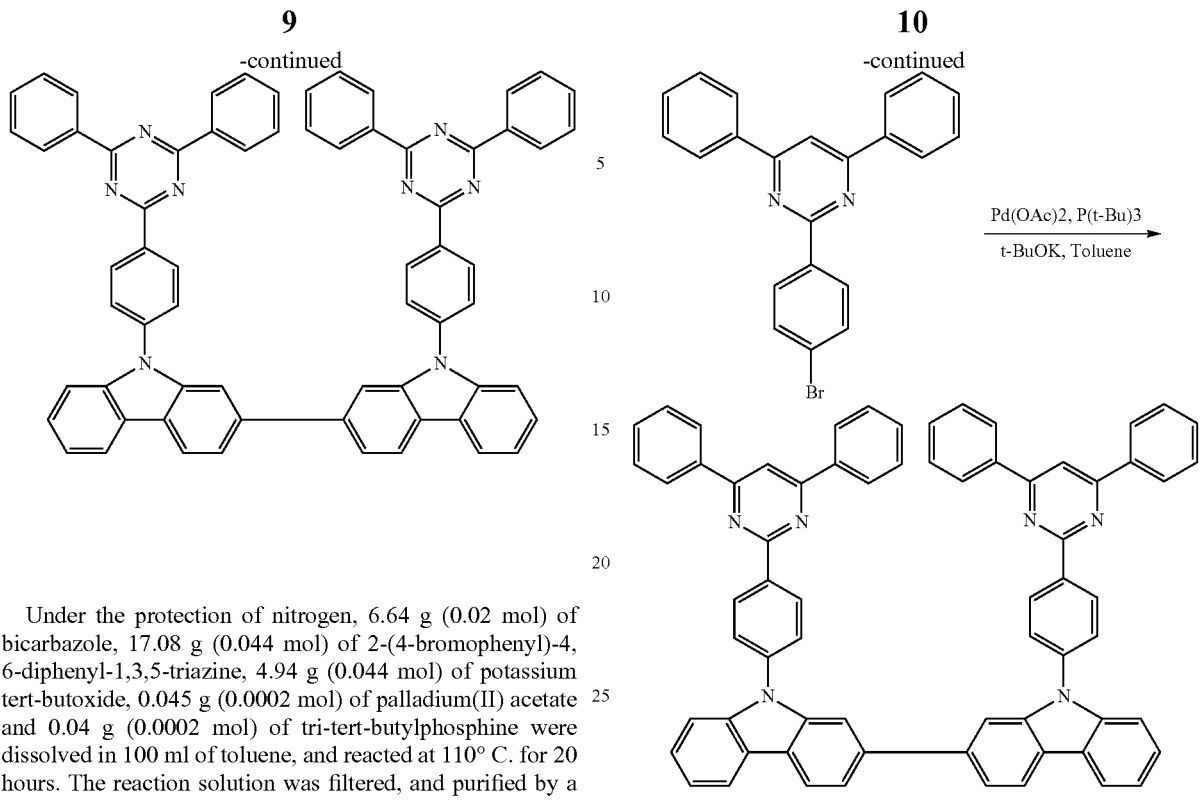

Under the protection of nitrogen, 6.64 g (0.02 mol) of bicarbazole, 17.08 g (0.044 mol) of 2-(4-bromophenyl)-4,6-diphenyl-1,3,5-triazine, 4.94 g (0.044 mol) of potassium tert-butoxide, 0.045 g (0.0002 mol) of palladium(II) acetate and 0.04 g (0.0002 mol) of tri-tert-butylphosphine were dissolved in 100 ml of toluene, and reacted at 110° C. for 20 hours. The reaction solution was filtered, and purified by a silica gel chromatography to obtain a crude product. The obtained solid was recrystallized with toluene, and then dried to obtain 14.96 g of compound 001 as off white solid with a yield of 79%.

The HPLC purity was greater than 99%. Mass spectrum: the calculated value was 947.09; and the test value was 947.08. Elemental analysis: the calculated values were C, 83.70%; H, 4.47%; N, 11.83%; the test value were C, 83.69%; H, 4.46%; N, 11.85%.

Preparation Example 2: The Synthesis of Compound 002

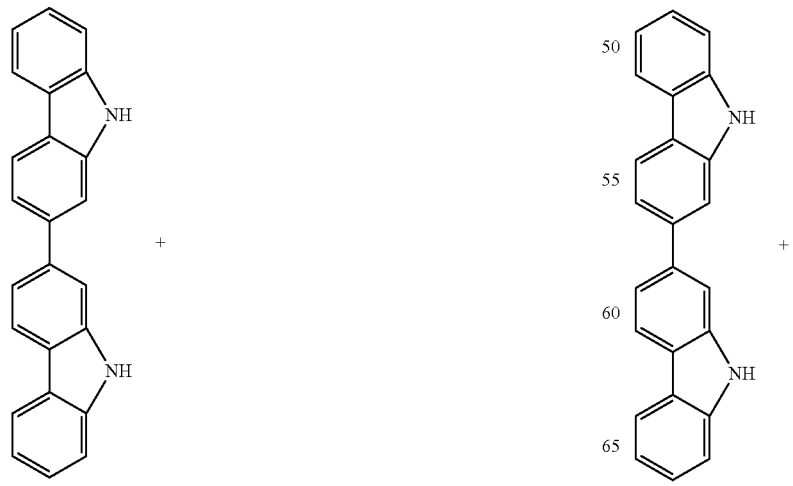

Under the protection of nitrogen, 6.64 g (0.02 mol) of bicarbazole, 17.04 g (0.044 mol) of 2-(4-bromophenyl)-4,6-diphenylpyrimidine, 4.94 g (0.044 mol) of potassium tert-butoxide, 0.045 g (0.0002 mol) of palladium(II) acetate and 0.04 g (0.0002 mol) of tri-tert-butylphosphine were dissolved in 100 ml of toluene, and reacted at 110° C. for 20 hours. The reaction solution was filtered, and purified by a silica gel chromatography to obtain a crude product. The obtained solid was recrystallized with toluene, and then dried to obtain 15.12 g of compound 002 as white solid with a yield of 80%.

The HPLC purity was greater than 99%. Mass spectrum: the calculated value was 945.12; and the test value was 945.12. Elemental analysis, the calculated values were C, 86.42%; H, 4.69%; N, 8.89%; the test value were C, 86.42%; H, 4.68%; N, 8.90%.

Preparation Example 3: The Synthesis of Compound 003

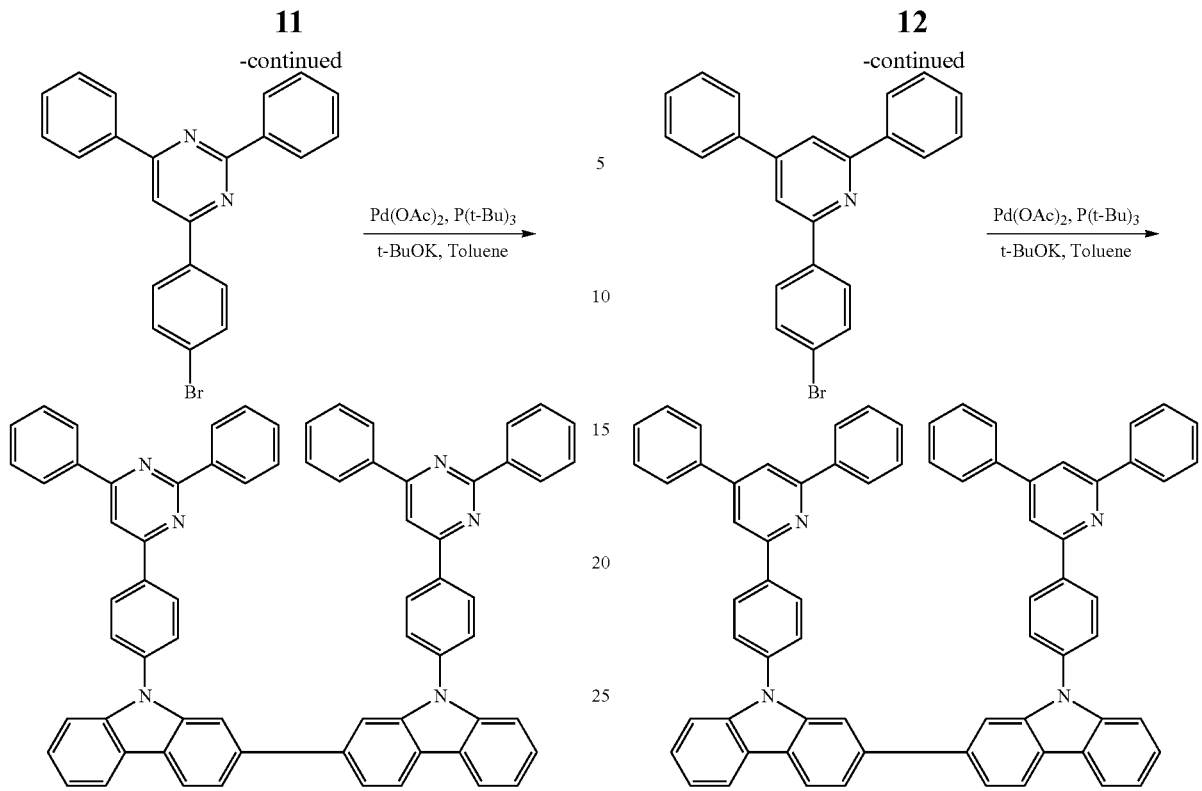

Under the protection of nitrogen, 6.64 g (0.02 mol) of bicarbazole, 17.04 g (0.044 mol) of 4-(4-bromophenyl)-2,6-diphenylpyrimidine, 4.94 g (0.044 mol) of potassium tert-butoxide, 0.045 g (0.0002 mol) of palladium(II) acetate and 0.04 g (0.0002 mol) of tri-tert-butylphosphine were dissolved in 100 ml of toluene, and reacted at 110° C. for 20 hours. The reaction solution was filtered, and purified by a silica gel chromatography to obtain a crude product. The obtained solid was recrystallized with toluene, and then dried to obtain 15.50 g of compound 003 as off white solid with a yield of 82%.

The HPLC purity was greater than 99%. Mass spectrum: the calculated value was 945.12; and the test value was 945.14. Elemental analysis, the calculated values were C, 86.42%; H, 4.69%; N, 8.89%; the test value were C, 86.41%; H, 4.68%; N, 8.89%.

Preparation Example 4: The Synthesis of Compound 004

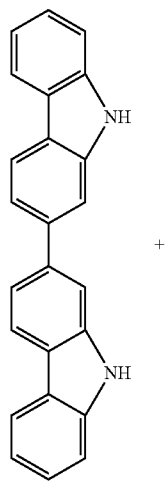

Under the protection of nitrogen, 6.64 g (0.02 mol) of bicarbazole, 17.00 g (0.044 mol) of 2-(4-bromophenyl)-4,6-diphenylpyridine, 4.94 g (0.044 mol) of potassium tert-butoxide, 0.045 g (0.0002 mol) of palladium(II) acetate and 0.04 g (0.0002 mol) of tri-tert-butylphosphine were dissolved in 100 ml of toluene, and reacted at 110° C. for 20 hours. The reaction solution was filtered, and purified by a silica gel chromatography to obtain a crude product. The obtained solid was recrystallized with toluene, and then dried to obtain 15.28 g of compound 004 as off white solid with a yield of 81%.

The HPLC purity was greater than 99%. Mass spectrum: the calculated value was 943.14; and the test value was 943.13. Elemental analysis, the calculated values were C, 89.14%; H, 4.92%; N, 5.94%; the test value were C, 89.16%; H, 4.91%; N, 5.93%.

As seen from the above results, the test results were consistent with the theoretical calculation results, which indicated that the prepared compounds 001-004 were just the compounds represented by the formulas 001-004.

Organic electroluminescent devices were prepared by using the compounds 001-004 prepared from the above preparation examples 001-004, and then compared with the comparative sample. In the organic electroluminescent devices, the compound of formula (I) can be used as a green phosphorescence host material, a hole-injecting material or a hole-transporting material. The invention was illustrated below by using the compound as a green phosphorescence host material.

Comparative Example 1

An organic electroluminescent device having the following structure as a comparative sample was prepared by using a compound of the following formula a as a phosphorescent host material for a light emitting layer, a compound of the following formula b as a doping material, 2-TNATA (4,4, 4-tri(N-naphthyl)-N-phenylamino)-triphenylamine) as a hole-injecting material, and α-NPD (N,N'-di(naphthyl)-N,N-diphenylbenzidine) as a hole-transporting material. ITO/2-TNATA (80 nm)/α-NPD (30 nm)/compound a+compound b (30 nm)/Alq₃ (30 nm)/LiF (0.5 nm)/Al (60 nm)

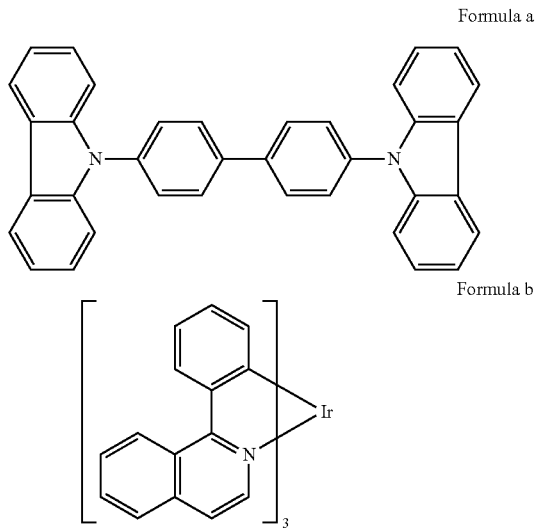

Formula a

Formula b

Specifically, a 15 Ω/cm² (1000 Å) ITO glass substrate from Corning Co. was cut into a size of 50 mm×50 mm×0.7 mm, and then in microwave, washed in acetone, isopropanol, purified water in turn for 15 minutes respectively, and then further washed in UV for 30 minutes. A hole injection layer was formed by vacuum depositing 2-TNATA having a thickness of 80 nm on the substrate. A hole transport layer was formed by vacuum depositing α-NPD having a thickness of 30 nm on the hole injection layer. A light-emitting layer was formed by vacuum depositing a compound represented by chemical formula a and a compound represented by chemical formula b (at a doping ratio of 10%) having a thickness of 30 nm on the hole transport layer. An electron transport layer was formed by vacuum depositing Alq₃ having a thickness of 30 nm on the light-emitting layer. An organic light-emitting device was prepared by vacuum depositing 0.5 nm LiF (electron injection) and 60 nm Al on the electron transport layer in turn. In this comparative example and the following application example, vacuum deposition was carried out by using an EL evaporation deposition machine manufactured by DOV Co. from Korean.

Application Examples 1-4

Organic light-emitting devices having a structure of ITO/2-TNATA (80 nm)/α-NPD (30 nm)/one of the green phosphorescent host compounds 001-004+b (30 nm, the doping rate of b was 10%)/Alq₃ (30 nm)/LiF (0.5 nm)/Al (60 nm) (that is, samples 1-4) were prepared by using the process in comparative example 1 with the exception that the compounds 001-004 were used for the phosphorescent host for the light-emitting layer instead of the compound a.

Testing Example 1: The Tests for the Luminescence Properties of the Comparative Sample and the Samples 1-4

The comparative sample and the samples 1-4 were tested for evaluating the driving voltage, luminance, luminous efficiency and luminous color by using Keithley2400 series digital source apparatus from the Taiwan Branch of American Keithley Instruments Inc., Konica Minolta konica minolta CS-2000, and CS-2000A photometer. The comparative sample and the samples 1-4 were subjected to the same tests. The results were listed in Table 1:

TABLE 1

| Samples | Host compound | Doping compound | Voltage OP. V | Brilliance [cd/m²] | Efficiency [cd/A] | Luminescence peak [nm] |
|---|---|---|---|---|---|---|
| Comparative sample | a | b | 6.72 | 2372 | 23.7 | 512 |
| 1 | 001 | b | 5.6 | 3516 | 35.16 | 513 |
| 2 | 002 | b | 5.9 | 3478 | 34.78 | 512 |
| 3 | 003 | b | 5.7 | 3609 | 36.09 | 515 |
| 4 | 004 | b | 5.1 | 3549 | 35.49 | 514 |

As indicated in Table 1, according to the samples 1 to 4 compared with the comparative sample, the above samples exhibited a green emission peak in the range 511-517 nm. The organic light emitting devices using the compounds of the present invention had significantly higher emission efficiencies.

In addition, organic light-emitting devices having a structure of ITO/2-TNATA (80 nm)+bicarbazole derivatives 001~004/α-NPD (30 nm)/compound a (30 nm, where b content was 8%)/Alq₃ (30 nm)/LiF (0.5 nm)/Al (60 nm) were prepared by using the process in comparative example 1 with the exception that the compounds 001-004 shown in the preparation examples were used for the compound for the hole injection layer instead of 2-TNATA. That is, these compounds 001-004 may be used as a hole-injecting material.

Organic light-emitting devices having a structure of ITO/2-TNATA (80 nm)/bicarbazole derivatives 001~004+α-NPD (30 nm)/compound a+b] (25 nm, where b content was 8.0%)/Alq₃(30 nm)/LiF (0.5 nm)/Al (60 nm) were prepared by using the process in comparative example 1 with the exception that the compounds 001-004 shown in the preparation examples were used for the compound for the hole transporting layer instead of α-NPD. That is, these compounds 001-004 may be used as a hole-transporting material.

Although the present invention has been specifically described and illustrated by using exemplary embodiments, it should be understood that those of ordinary skill may take various changes in form and details without departing from the spirit and scope of the invention as defined by the following claims.

What is claimed is:

1. A light emitting layer comprising:
a bicarbazole derivative represented by the following molecular structure as a phosphorescent host material:

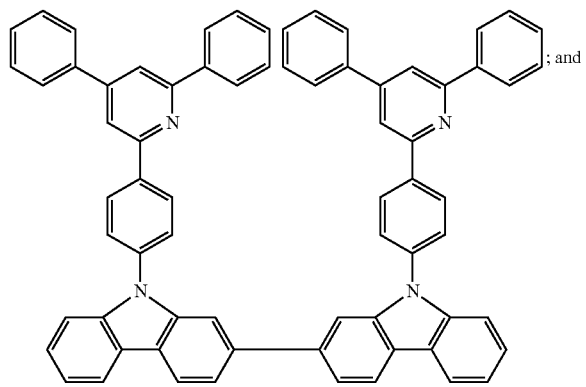 [SMILES: c1ccc(-c2cc(-c3ccccc3)nc(-c3ccc(-n4c5ccccc5c5ccc(-c6ccc7c8ccccc8n(-c8ccc(-c9cc(-c%10ccccc%10)cc(-c%10ccccc%10)n9)cc8)c7c6)cc54)cc3)c2)cc1]

; and a compound of the following formula b as a doping material:

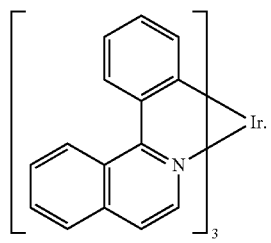

(b)

2. An organic electroluminescent device, comprising a first electrode, a second electrode and one or more organic compound layer(s) provided between the first electrode and the second electrode, wherein at least one organic compound layer comprises at least one bicarbazole derivative according to claim 1, and the compound of the formula b as a doping material according to claim 1.

3. The organic electroluminescent device according to claim 2, wherein the bicarbazole derivative is a phosphorescence host material.

4. The organic electroluminescent device according to claim 3, wherein the bicarbazole derivative is a green phosphorescence host material.

5. The organic electroluminescent device according to claim 2, wherein the bicarbazole derivative is a hole-injecting material.

6. The organic electroluminescent device according to claim 2, wherein the bicarbazole derivative is a hole-transporting material.

* * * * *